US011484480B2

(12) United States Patent
Verhovnik et al.

(10) Patent No.: US 11,484,480 B2
(45) Date of Patent: Nov. 1, 2022

(54) HAIR COLORING COMPOSITION COMPRISING MICROCAPSULES

(71) Applicant: FIRMENICH SA, Satigny (CH)

(72) Inventors: Glenn Verhovnik, Satigny (CH); Arnaud Struillou, Satigny (CH); John Callf, Singapore (SG)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/766,234

(22) PCT Filed: Jan. 24, 2019

(86) PCT No.: PCT/EP2019/051743
§ 371 (c)(1),
(2) Date: May 21, 2020

(87) PCT Pub. No.: WO2019/145416
PCT Pub. Date: Aug. 1, 2019

(65) Prior Publication Data
US 2020/0368121 A1 Nov. 26, 2020

(30) Foreign Application Priority Data

Jan. 26, 2018 (EP) .................................. 18153663

(51) Int. Cl.
A61K 8/11 (2006.01)
A61K 8/41 (2006.01)
A61K 8/87 (2006.01)
A61Q 5/10 (2006.01)
A61Q 5/12 (2006.01)
A61Q 13/00 (2006.01)

(52) U.S. Cl.
CPC .............. A61K 8/11 (2013.01); A61K 8/411 (2013.01); A61K 8/87 (2013.01); A61Q 5/10 (2013.01); A61Q 5/12 (2013.01); A61Q 13/00 (2013.01); A61K 2800/622 (2013.01); A61K 2800/624 (2013.01); A61K 2800/652 (2013.01)

(58) Field of Classification Search
CPC . A61Q 13/00; A61Q 5/02; A61Q 5/10; A61Q 5/12; A61Q 5/00; A61K 8/411; A61K 8/11; A61K 8/87; A61K 2800/622; A61K 2800/652; A61K 2800/56
See application file for complete search history.

(56) References Cited

U.S. PATENT DOCUMENTS

| 5,756,106 A * | 5/1998 | Concannon | A61K 8/03 |
| | | | 424/401 |
| 5,993,791 A | 11/1999 | Cotteret et al. | |
| 7,320,711 B2 | 1/2008 | Schmenger et al. | |
| 2010/0288968 A1* | 11/2010 | Lin | C09C 1/00 |
| | | | 252/75 |
| 2016/0184196 A1* | 6/2016 | Baxter | A61K 9/501 |
| | | | 424/401 |

FOREIGN PATENT DOCUMENTS

| DE | 4342009 A1 | 6/1995 | |
| DE | 10347243 A1 | 5/2005 | |
| EP | 0818192 A1 * | 1/1998 | ............... A61Q 5/10 |
| EP | 0946133 A1 | 10/1999 | |
| EP | 2300146 A1 | 3/2011 | |
| EP | 2579976 A1 | 4/2013 | |
| WO | 2007004166 A1 | 1/2007 | |
| WO | 2012084916 A1 | 6/2012 | |
| WO | 2013068255 A1 | 5/2013 | |
| WO | 2013092375 A1 | 6/2013 | |
| WO | 2015110568 A1 | 7/2015 | |
| WO | 2016054351 A1 | 4/2016 | |
| WO | WO-2016054351 A1 * | 4/2016 | ............. A61Q 19/10 |
| WO | 2016116604 A1 | 7/2016 | |
| WO | WO-2016116604 A1 * | 7/2016 | ............... A61K 8/11 |
| WO | 2018019894 A1 | 2/2018 | |
| WO | 2018115250 A1 | 6/2018 | |

OTHER PUBLICATIONS

International Search Report and Written Opinion for corresponding PCT/EP2019/051743 dated Mar. 7, 2019, 13 pages.
Vuilleumier et al., Multidimensional Visualization of Physical and Perceptual Data Leading to a Creative Approach in Fragrance Development, Perfume & Flavorist, vol. 33, Sep. 2008, pp. 54-61.

* cited by examiner

Primary Examiner — Blessing M Fubara
(74) Attorney, Agent, or Firm — Armstrong Teasdale LLP

(57) ABSTRACT

The present disclosure relates to the field of hair coloring compositions. Described herein is an oxidative hair coloring composition including microcapsules made of a perfumed-oil based core and a polymeric shell. Also described herein are a method for coloring hair and a hair coloring kit.

14 Claims, No Drawings

HAIR COLORING COMPOSITION COMPRISING MICROCAPSULES

CROSS-REFERENCE TO RELATED APPLICATIONS

This application is a U.S. National Phase Application of PCT/EP2019/051743, filed on Jan. 24, 2019, which claims the benefit of priority to European Patent Application Number 18153663.2, filed Jan. 26, 2018, the entire contents of which are hereby incorporated by reference herein.

TECHNICAL FIELD

The present invention relates to the field of hair coloring compositions. It concerns more particularly an oxidative hair coloring composition comprising microcapsules made of a perfumed-oil based core and a polymeric shell. A method for coloring hair and a hair coloring kit are also objects of the invention.

BACKGROUND OF THE INVENTION

Delivery systems containing a perfume, to release the fragrance in a controlled manner are commonly used in the perfumery industry and well documented in the art.

The increasing consumer demand for an intense and strong perfume release (i.e good olfactive performance) during and after usage is driving the development of new delivery systems.

In addition, these systems have to survive in challenging bases without physically dissociating or degrading. This is referred to as performance in terms of stability for the delivery system.

Depending on the consumer product, the consumer base will be more or less aggressive.

Among consumer products comprising a very aggressive medium, one may cite for example hair dying systems.

Indeed, hair dying systems are divided in two main categories, oxidative and non-oxidative systems and also according to the color durability after application (temporary or permanent).

Permanent hair dyes, also called oxidative hair dyes, are commonly used because they provide greater efficacy of dyeing, and are resistant to shampoo.

They are generally marketed as two-component kits. One component contains a dye precursor and a coupling agent in an alkaline base, and the other component is a stabilized solution of hydrogen peroxide. The two components are mixed immediately prior to use.

Most of the permanent systems comprise ammonium hydroxide in the alkaline base. However, upon mixing of the 2 phases, some ammonia is released and this generates an unpleasant perception by the user upon mixing and can leave an unpleasant smell on hair during the application and even after rinsing of the application on the hair. Consequently, perfume is often added in hair dying compositions to try to cover this ammonia malodour.

When the fragrances are present as a free oil, the main challenges are the enhanced fragrance performance and the long-lasting of the olfactive perception during and after use, e.g. after rinsing and drying of the hair. Furthermore, hair dying compositions contains high levels of aggressive components that are very challenging for the stability of the perfume, greatly limiting the palette of raw materials a perfumer can use.

There is therefore a need to provide an oxidative hair coloring composition that would release perfume not only on hair after its application (e.g. after rinsing and drying of the hair) but also during the application, said perfume being stable in the hair coloring composition.

The present invention is proposing a solution to the above-mentioned problem, based on a hair coloring composition comprising perfume encapsulated in core-shell microcapsules having a size greater than 25 microns. The encapsulation would provide protection of the perfume from degradation by the aggressive ingredients of the base outside the microcapsules. Furthermore, the right size of the microcapsule helps release of the perfume upon application.

SUMMARY OF THE INVENTION

A first object of the invention is an oxidative hair coloring composition comprising:
(i) an oxidizing phase comprising an oxidizing agent;
(ii) an alkaline phase comprising an alkaline agent, a dye precursor and a coupling compound; and
(iii) core-shell microcapsules having a polymeric shell and a core comprising a perfume oil, said microcapsules having a mean size equal or greater than 25 microns.

A second object of the invention is a hair coloring kit comprising:
(i) a first container comprising an oxidizing agent; and
(ii) a second container comprising an alkalizing agent, a precursor dye and a coupling compound;
characterized in that the first and/or the second container further comprises core-shell microcapsules having a polymeric shell and a core comprising encapsulated perfume oil, said microcapsules having a mean size equal or greater than 25 microns.

A third object of the invention is a method for coloring hair comprising the step of:
a) applying the hair coloring composition as defined above on hair,
b) allowing the hair to stand, and
c) washing the hair with a shampoo.

DETAILED DESCRIPTION OF THE INVENTION

Unless stated otherwise, percentages (%) are meant to designate percent by weight of a composition.

According to the invention, "encapsulated oil" refers to oil that is encapsulated in a core-shell microcapsule.

By "core-shell microcapsule", or the similar, in the present invention it is meant that capsules have a particle size distribution in the micron range (e.g. a mean diameter (d(v, 0.5)) equal or greater than 25 microns, preferably equal or greater than 30 microns, preferably equal or greater than 70 microns, preferably equal or greater than 100 microns, even more preferably equal or greater than 150 microns and comprise an external polymeric shell and an internal continuous oil phase enclosed by the external shell. According to an embodiment, microcapsules have a mean size comprised between 25 and 2000 microns, preferably between 100 and 500 microns, more preferably between 150 and 500 microns.

According to the invention, the wordings "mean diameter" or "mean size" are used indifferently.

Mean sizes were measured by a laser diffraction particle size analyzer.

The present inventors have surprisingly discovered that the release of the perfume is particularly advantageous with microcapsules having a mean size equal or greater than 25 microns, preferably equal or greater than 100 microns, since an instantaneous fragrance release burst (or blooming) can be obtained from the encapsulated oil by mechanical action when the user applies the hair coloring composition onto hair and upon lathering. Furthermore, a long-lasting effect can be also perceived by the user after application.

A first object of the invention is therefore an oxidative hair coloring composition comprising:
  (i) an oxidizing phase comprising an oxidizing agent;
  (ii) an alkaline phase comprising an alkaline agent, a dye precursor and a coupling compound;
    characterized in that the coloring composition comprises core-shell microcapsules having a polymeric shell and a core comprising a perfume oil, said microcapsules having a mean size equal or greater than 25 microns.

It should be understood that, according to the invention, the dye precursor and the coupling compound form an oxidative hair dye in the presence of the oxidizing agent.

The hair coloring composition comprises the microcapsules in the oxidizing phase and/or the alkaline phase.

One of the essential features of the invention is the presence of microcapsules having a size equal or greater than 25 microns.

The microcapsules of the invention show good performance in terms of blooming and long lasting effect which translate into good odor performance. In this regard it has to be mentioned that although ideal situation would be one where microcapsules show best performance in blooming, combine with the best performance on dry hair, different scenarios can be very interesting depending on the application and capsules with a slightly less blooming performance with higher long-lasting performance can be very useful and vice-versa. The capsules of the invention have a profile blooming/long lasting performance that varies depending on the size of the microcapsules. A skilled person in the art is capable of choosing the best balance depending on the needs in application.

As a non-limited example, microcapsules having a mean size comprised between 25 and 70 microns, have proved optimal for long-lastingness and microcapsules having a mean size greater than 100 microns, preferably between 100 and 500 microns have proved optimal for blooming.

Core-Shell Microcapsules

Oil-Based Core

According to the invention, the oil-based core comprises a perfume.

According to a particular embodiment, the oil-based core comprises a mixture of a perfume with another ingredient selected from the group consisting of nutraceuticals, cosmetics, insect control agents and biocide actives.

According to a particular embodiment, the oil-based core consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, the perfume oil also includes the combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability or insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate.

According to an embodiment, the oil-based core comprises:
  25-100 wt % of a perfume oil comprising at least 15 wt % of high impact perfume raw materials having a Log T<−4, and
  0-75 wt % of a density balancing material having a density greater than 1.07 $g/cm^3$.

The odor threshold concentration of a perfuming compound is determined by using a gas chromatograph ("GC"). Specifically, the gas chromatograph is calibrated to determine the exact volume of the perfume oil ingredient injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and hence the concentration of the perfuming compound. To determine the threshold concentration, solutions are delivered to the sniff port at the back-calculated concentration. A panelist sniffs the GC effluent and identifies the retention time when odor is noticed. The average across all panelists determines the odor threshold concentration of the perfuming compound. The determination of odor threshold is described in more detail in C. Vuilleumier et al., Multidimensional Visualization of Physical and Perceptual Data Leading to a Creative Approach in Fragrance Development, Perfume & Flavorist, Vol. 33, September, 2008, pages 54-61.

The nature of high impact perfume raw materials having a Log T<−4 and density balancing material having a density greater than 1.07 $g/cm^3$ are described in WO2018115250, the content of which are included by reference.

According to an embodiment, the high impact perfume raw materials having a Log T<−4 are selected from the list in Table A below.

TABLE A high impact perfume raw materials having a Log T < −4
Perfume raw materials (Log T < −4)

(+−)-1-METHOXY-3-HEXANETHIOL
4-(4-HYDROXY-1-PHENYL)-2-BUTANONE
(+−)-2-(4-METHYL-3-CYCLOHEXEN-1-YL)-2-PROPANETHIOL
2-METHOXY-4-(1-PROPENYL)-1-PHENYL ACETATE
PYRAZOBUTYLE
3-PROPYLPHENOL
1-(3-METHYL-1-BENZOFURAN-2-YL)ETHANONE
2-(3-PHENYLPROPYL)PYRIDINE
1-(3,3-DIMETHYL-1-CYCLOHEXEN-1-YL)-4-PENTEN-1-ONE (A) + (5,5-DIMETHYL-1-CYCLOHEXEN-1-YL)-4-PENTEN-1-ONE (B)
1-(5,5-DIMETHYL-1-CYCLOHEXEN-1-YL)-4-PENTEN-1-ONE
(3RS,3ARS,6SR,7ASR)-PERHYDRO-3,6-DIMETHYL-BENZO[B]FURAN-2-ONE (A) + (3SR,3ARS,6SR,7ASR)-PERHYDRO-3,6-DIMETHYL-BENZO[B]FURAN-2-ONE (B)
(+−)-1-(5-ETHYL-5-METHYL-1-CYCLOHEXEN-1-YL)-4-PENTEN-1-ONE
(1'S,3'R)-1-METHYL-2-[(1',2',2'-TRIMETHYLBICYCLO[3.1.0]HEX-3'-YL)METHYL]CYCLOPROPYL}METHANOL
(+−)-3-MERCAPTOHEXYL ACETATE
(2E)-1-(2,6,6-TRIMETHYL-1,3-CYCLOHEXADIEN-1-YL)-2-BUTEN-1-ONE
7-METHYL-2H-1,5-BENZODIOXEPIN-3(4H)-ONE
(2E,6Z)-2,6-NONADIEN-1-OL
(4Z)-4-DODECENAL
(+−)-4-HYDROXY-2,5-DIMETHYL-3(2H)-FURANONE
METHYL 2,4-DIHYDROXY-3,6-DIMETHYLBENZOATE
3-METHYLINDOLE
(+−)-PERHYDRO-4ALPHA,8ABETA-DIMETHYL-4A-NAPHTHALENOL
PATCHOULOL
2-METHOXY-4-(1-PROPENYL)PHENOL
(+−)-5,6-DIHYDRO-4-METHYL-2-PHENYL-2H-PYRAN (A) + TETRAHYDRO-4-METHYLENE-2-PHENYL-2H-PYRAN (B)
4-METHYLENE-2-PHENYLTETRAHYDRO-2H-PYRAN (A) + (+−)-4-METHYL-2-PHENYL-3,6-DIHYDRO-2H-PYRAN (B)
4-HYDROXY-3-METHOXYBENZALDEHYDE
NONYLENIC ALDEHYDE
2-METHOXY-4-PROPYLPHENOL
(2Z)-3-METHYL-5-PHENYL-2-PENTENENITRILE (A) + (2E)-3-METHYL-5-PHENYL-2-PENTENENITRILE (B)
1-(SPIRO[4.5]DEC-6-EN-7-YL)-4-PENTEN-1-ONE (A) + 1-(SPIRO[4.5]DEC-7-EN-7-YL)-4-PENTEN-1-ONE (B)
2-METHOXYNAPHTHALENE
(−)-(3AR,5AS,9AS,9BR)-3A,6,6,9A-TETRAMETHYLDODECAHYDRONAPHTHO[2,1-B]FURAN
5-NONANOLIDE
(3AR,5A5,9A5,9BR)-3A,6,6,9A-TETRAMETHYLDODECAHYDRONAPHTHO[2,1-B]FURAN
7-ISOPROPYL-2H,4H-1,5-BENZODIOXEPIN-3-ONE
COUMARIN
4-METHYLPHENYL ISOBUTYRATE
(2E)-1-(2,6,6-TRIMETHYL-1,3-CYCLOHEXADIEN-1-YL)-2-BUTEN-1-ONE
BETA,2,2,3-TETRAMETHYL-DELTA-METHYLENE-3-CYCLOPENTENE-1-BUTANOL
DELTA DAMASCONE ((2E)-1-[(1RS,2SR)-2,6,6-TRIMETHYL-3-CYCLOHEXEN-1-YL]-2-BUTEN-1-ONE)
(+−)-3,6-DIHYDRO-4,6-DIMETHYL-2-PHENYL-2H-PYRAN
ANISALDEHYDE
PARACRESOL
3-ETHOXY-4-HYDROXYBENZALDEHYDE
METHYL 2-AMINOBENZOATE
ETHYL METHYLPHENYLGLYCIDATE
OCTALACTONE G
ETHYL 3-PHENYL-2-PROPENOATE
(−)-(2E)-2-ETHYL-4-[(1R)-2,2,3-TRIMETHYL-3-CYCLOPENTEN-1-YL]-2-BUTEN-1-OL
PARACRESYL ACETATE
DODECALACTONE
TRICYCLONE
(+)-(3R,5Z)-3-METHYL-5-CYCLOPENTADECEN-1-ONE
UNDECALACTONE
(1R,4R)-8-MERCAPTO-3-P-MENTHANONE
(3S,3A5,6R,7AR)-3,6-DIMETHYLHEXAHYDRO-1-BENZOFURAN-2(3H)-ONE
BÉTA IONONE
(+−)-6-PENTYLTETRAHYDRO-2H-PYRAN-2-ONE
(3E,5Z)-1,3,5-UNDECATRIENE
10-UNDECENAL (A) + (9E)-9-UNDECENAL (B) + (9Z)-9-UNDECENAL (C)
(Z)-4-DECENAL
(+−)-ETHYL 2-METHYLPENTANOATE
1,2-DIALLYLDISULFANE

TABLE A-continued high impact perfume raw materials having a Log T < −4
Perfume raw materials (Log T < −4)

(2Z)-2-TRIDECENENITRILE (A) + (3Z)-3-TRIDECENENITRILE (B) + (3E)-3-TRIDECENENITRILE (C) + (2E)-2-TRIDECENENITRILE (D)
(+−)-2-ETHYL-4,4-DIMETHYL-1,3-OXATHIANE
(+)-(3R,5Z)-3-METHYL-5-CYCLOPENTADECEN-1-ONE
3-(4-TERT-BUTYLPHENYL)PROPANAL
ALLYL (CYCLOHEXYLOXY)ACETATE
METHYLNAPHTHYLKETONE
(+−)-(4E)-3-METHYL-4-CYCLOPENTADECEN-1-ONE (A) + (+−)-(5E)-3-METHYL-5-CYCLOPENTADECEN-1-ONE (B) + (+−)-(5Z)-3-METHYL-5-CYCLOPENTADECEN-1-ONE (C)
CYCLOPROPYLMETHYL (3Z)-3-HEXENOATE (A) + CYCLOPROPYLMETHYL (3E)-3-HEXENOATE (B)
(4E)-4-METHYL-5-(4-METHYLPHENYL)-4-PENTENAL
(+−)-1-(5-PROPYL-1,3-BENZODIOXOL-2-YL)ETHANONE
4-METHYL-2-PENTYLPYRIDINE
(+−)-(E)-3-METHYL-4-(2,6,6-TRIMETHYL-2-CYCLOHEXEN-1-YL)-3-BUTEN-2-ONE
(3ARS,5ASR,9ASR,9BRS)-3A,6,6,9A-PETRAMETHYLDODECAHYDRONAPHTHO[2,1-B]FURAN
(2S,5R)-5-METHYL-2-(2-PROPANYL)CYCLOHEXANONE OXIME
6-HEXYLTETRAHYDRO-2H-PYRAN-2-ONE
(+−)-3-(3-ISOPROPYL-1-PHENYL)BUTANAL
METHYL 2-((1RS,2RS)-3-OXO-2-PENTYLCYCLOPENTYL)ACETATE (A) + METHYL 2-((1RS,2SR)-3-OXO-2-PENTYLCYCLOPENTYL)ACETATE (B)
1-(2,6,6-TRIMETHYL-1-CYCLOHEX-2-ENYL)PENT-1-EN-3-ONE
INDOL
7-PROPYL-2H,4H-1,5-BENZODIOXEPIN-3-ONE
ETHYL PRALINE
(4-METHYLPHENOXY)ACETALDEHYDE
ETHYL TRICYCLO[5.2.1.0.(2,6)]DECANE-2-CARBOXYLATE
(+)-(1'S,2S,E)-3,3-DIMETHYL-5-(2',2',3'-TRIMETHYL-3'-CYCLOPENTEN-1'-YL)-4-PENTEN-2-OL
(2R,4E)-3,3-DIMETHYL-5-[(1R)-2,2,3-TRIMETHYL-3-CYCLOPENTEN-1-YL]-4-PENTEN-2-OL (A) + (2S,4E)-3,3-DIMETHYL-5-[(1R)-2,2,3-TRIMETHYL-3-CYCLOPENTEN-1-YL]-4-PENTEN-2-OL (B)
8-ISOPROPYL-6-METHYL-BICYCLO[2.2.2]OCT-5-ENE-2-CARBALDEHYDE
METHYLNONYLACETALDEHYDE
4-FORMYL-2-METHOXYPHENYL 2-METHYLPROPANOATE
(E)-4-DECENAL
(+−)-2-ETHYL-4-(2,2,3-TRIMETHYL-3-CYCLOPENTEN-1-YL)-2-BUTEN-1-OL
(1R,5R)-4,7,7-TRIMETHYL-6-THIABICYCLO[3.2.1]OCT-3-ENE (A) + (1R,4R,5R)-4,7,7-TRIMETHYL-6-THIABICYCLO[3.2.1]OCTANE (B)
(−)-(3R)-3,7-DIMETHYL-1,6-OCTADIEN-3-OL
(E)-3-PHENYL-2-PROPENENITRILE
4-METHOXYBENZYL ACETATE
(E)-3-METHYL-5-(2,2,3-TRIMETHYL-3-CYCLOPENTEN-1-YL)-4-PENTEN-2-OL
ALLYL (3-METHYLBUTOXY)ACETATE (A) + (+−)-ALLYL (2-METHYLBUTOXY)ACETATE
(+−)-(2E)-1-(2,6,6-TRIMETHYL-2-CYCLOHEXEN-1-YL)-2-BUTEN-1-ONE
(1E)-1-(2,6,6-TRIMETHYL-1-CYCLOHEXEN-1-YL)-1-PENTEN-3-ONE

According to an embodiment, perfume raw materials having a Log T<−4 are chosen in the group consisting of aldehydes, ketones, alcohols, phenols, esters lactones, ethers, epoxydes, nitriles and mixtures thereof.

According to an embodiment, perfume raw materials having a Log T<−4 comprise at least one compound chosen in the group consisting of alcohols, phenols, esters lactones, ethers, epoxydes, nitriles and mixtures thereof, preferably in amount comprised between 20 and 70% by weight based on the total weight of the perfume raw materials having a Log T<−4.

According to an embodiment, perfume raw materials having a Log T<−4 comprise between 20 and 70% by weight of aldehydes, ketones, and mixtures thereof based on the total weight of the perfume raw materials having a Log T<−4.

The remaining perfume raw materials contained in the oil-based core may have therefore a Log T>−4.

Non limiting examples of perfume raw materials having a Log T>−4 are listed in table B below.

TABLE B perfume raw materials having a Log T > −4
Perfume raw materials (Log T > −4)

ETHYL 2-METHYLBUTYRATE
(E)-3-PHENYL-2-PROPENYL ACETATE
(+−)-8-SEC-BUTYLQUINOLINE (A) + (+−)-6-SEC-BUTYLQUINOLINE
(+−)-3-(1,3-BENZODIOXOL-5-YL)-2-METHYLPROPANAL
VERDYLE PROPIONATE
1-(OCTAHYDRO-2,3,8,8-TETRAMETHYL-2-NAPHTALENYL)-1-ETHANONE
METHYL 2-((1RS,2RS)-3-OXO-2-PENTYLCYCLOPENTYL)ACETATE
(+−)-(E)-4-METHYL-3-DECEN-5-OL
2,4-DIMETHYL-3-CYCLOHEXENE-1-CARBALDEHYDE
1,3,3-TRIMETHYL-2-OXABICYCLO[2.2.2]OCTANE
TETRAHYDRO-4-METHYL-2-(2-

TABLE B-continued perfume raw materials having a Log T > −4
Perfume raw materials (Log T > −4)

METHYL-1-PROPENYL)-2H-PYRAN
ALDEHYDE C 12
1-OXA-12-CYCLOHEXADECEN-2-ONE
(A) + 1-OXA-13-CYCLOHEXADECEN-2-
ONE (B)
(+−)-3-(4-ISOPROPYLPHENYL)-2-
METHYLPROPANAL
ALDEHYDE C 11 LENIQUE
(+−)-2,6-DIMETHYL-7-OCTEN-2-OL
(+−)-2,6-DIMETHYL-7-OCTEN-2-OL
ALLYL 3-CYCLOHEXYLPROPANOATE
(Z)-3-HEXENYL ACETATE
(2RS,5SR)-5-METHYL-2-(2-
PROPANYL)CYCLOHEXANONE (A) +
(2RS,5RS)-5-METHYL-2-(2-
PROPANYL)CYCLOHEXANONE (B)
ALLYL HEPTANOATE
(1RS,2RS)-2-(2-METHYL-2-
PROPANYL)CYCLOHEXYL ACETATE (A) +
(1RS,2SR)-2-(2-METHYL-2-
PROPANYL)CYCLOHEXYL ACETATE (B)
1,1-DIMETHYL-2-PHENYLETHYL
BUTYRATE
GERANYL ACETATE (A) + NERYL
ACETATE (B)
(+−)-1-PHENYLETHYL ACETATE
1,1-DIMETHYL-2-PHENYLETHYL
ACETATE
3-METHYL-2-BUTENYL ACETATE
ETHYL 3-OXOBUTANOATE (A) <=> (2Z)-
ETHYL 3-HYDROXY-2-BUTENOATE (B)
8-P-MENTHANOL
8-P-MENTHANYLACETATE (A) + 1-P-
MENTHANYL ACETATE (B)
(+−)-2-(4-METHYL-3-CYCLOHEXEN-1-
YL)-2-PROPANYL ACETATE
(+−)-2-METHYLBUTYL BUTANOATE
2-{(1S)-1-[(1R)-3,3-
DIMETHYLCYCLOHEXYL]ETHOXY}-2-
OXOETHYL PROPIONATE
3,5,6-TRIMETHYL-3-CYCLOHEXENE-1-
CARBALDEHYDE (A) + 2,4,6-
TRIMETHYL-3-CYCLOHEXENE-1-
CARBALDEHYDE (B)
2-CYCLOHEXYLETHYL ACETATE
ALDEHYDE C 8
ETHYL BUTANOATE
(+−)-(3E)-4-(2,6,6-TRIMETHYL-2-
CYCLOHEXEN-1-YL)-3-BUTEN-2-ONE
(A) + (3E)-4-(2,6,6-TRIMETHYL-1-
CYCLOHEXEN-1-YL)-3-BUTEN-2-ONE
(B);
1-[(1RS,6SR)-2,2,6-
TRIMETHYLCYCLOHEXYL]-3-HEXANOL
1,3,3-TRIMETHYL-2-
OXABICYCLO[2.2.2]OCTANE
1,3,3-TRIMETHYL-2-
OXABICYCLO[2.2.2]OCTANE
ETHYL HEXANOATE
UNDECANAL
ALDEHYDE C 10
2-PHENYLETHYL ACETATE
(1S,2S,4S)-1,7,7-
TRIMETHYLBICYCLO[2.2.1]HEPTAN-2-
OL (A) + (1S,2R,4S)-1,7,7-
TRIMETHYLBICYCLO[2.2.1]HEPTAN-2-
OL (B)
(+−)-3,7-DIMETHYL-3-OCTANOL
1-METHYL-4-(2-
PROPANYLIDENE)CYCLOHEXENE
(+)-(R)-4-(2-METHOXYPROPAN-2-YL)-1-
METHYLCYCLOHEX-1-ENE
VERDYL ACETATE
(3R)-1-[(1R,6S)-2,2,6-
TRIMETHYLCYCLOHEXYL]-3-
HEXANOL (A) + (3S)-1-[(1R,6S)-2,2,6-
TRIMETHYLCYCLOHEXYL]-3-

TABLE B-continued perfume raw materials having a Log T > −4
Perfume raw materials (Log T > −4)

HEXANOL (B) + (3R)-1-[(1S,6S)-2,2,6-
TRIMETHYLCYCLOHEXYL]-3-
HEXANOL (C)
(+)-(1S,1'R)-2-[1-(3',3'-DIMETHYL-1'-
CYCLOHEXYL)ETHOXY]-2-
METHYLPROPYL PROPANOATE

According to an embodiment, the oil-based core comprises 2-75 wt % of a density balancing material having a density greater than 1.07 g/cm³.

The density of a component is defined as the ratio between its mass and its volume (g/cm³).

Several methods are available to determine the density of a component.

One may refer for example to the ISO 298:1998 method to measure d20 densities of essential oils.

According to an embodiment, the density balancing material is chosen in the group consisting of benzyl salicylate, benzyl benzoate, cyclohexyl salicylate, benzyl phenylacetate, phenylethyl phenoxyacetate, triacetin, methyl and ethyl salicylate, benzyl cinnamate, and mixtures thereof.

According to a particular embodiment, the density balancing material is chosen in the group consisting of benzyl salicylate, benzyl benzoate, cyclohexyl salicylate and mixtures thereof.

According to another embodiment, the perfume comprises at least one perfume raw material chosen in the group consisting of aldehydes, ketones and mixture thereof, preferably in an amount comprised between 20 and 70% by weight based on the total weight of the perfume oil.

As non-limiting examples of aldehydes that can be used according to the present invention, one may cite aldehyde C6, aldehyde C7, aldehyde C8, aldehyde C9, aldehyde C10, aldehyde C11, aldehyde C12, undecenal, aldehyde methyloctylacetique, aldehyde mna, aldehyde supra, aldehyde tridecylenique, aldehyde nonylenique, cis nonenal, citral, citronellal, costenal (9-decenal), decenal, dimethylheptenal, dodecenal, dodecisal, heptenal, herbaldehyde, hexenal, melonal (2,6-Dimethylhept-5-enal), nonadienal, nonadienal, nonanal, pelargodienal, tangerinal ((4z)-4-dodecenal), trans-decenal, undecenal, Virisal® (3,7-dimethyloctanal), acropal, cyclovertal, Farenal® (2,6,10-trimethylundec-9-enal), isocyclocitral, isofreshal ((5 or 6)-methyl-(7 or 8)-(1-methylethyl)bicyclo[2.2.2]oct-5-ene-2-carbaldehyde), Liminal®, nonanal, octanal, trans-2 hexenal, trimenal, trivertal, zestover (2,4-dimethyl-3-cyclohexene-1-carbaldehyde), aldehyde amylcinnamique, aldehyde benzoique, aldehyde cinnamique, aldehyde hexylcinnamique, aldehyde phenylpropionique, aldehyde benzoique, cyclosal, florhydral, mimosal, Trifernal® ((+−)-3-phenylbutanal), floralozone, hivernal, Hivernal® neo, bourgeonal, lilial, Vulcanolide®, isobutavan, aldehyde anisique, foliaver, humusal, ethylvanilline, vanillin, heliopropanal, heliotropine, pinoacetaldehyde, mysoral, safranal, Tillenal®, herbaldehyde, Scentenal®, aldehyde muguet 50 (2-(3,7-dimethyloct-6-enoxy) acetaldehyde), precyclemone B and mixtures thereof.

As non-limiting examples of ketones that can be used according to the present invention, one may cite methylheptylcetone, ethylamylcetone, ethylpentylcetone, ethyl vinyl cetone, koavone, methylheptenone, methylhexylcetone, methylpentylcetone, mulantone, delta damascone, alpha damascone, damascenone, Iralia® total (Ionone methyl), Neobutenone® alpha, Iso E super (1-(octahydro-2,3,8,8- tetramethyl-2-naphtalenyl)-1-ethanone); Violet BC ((3E)-4-(2,6,6-trimethyl-1-cyclohexen-1-yl)-3-buten-2-one), Violet AT and mixtures thereof.

According to another embodiment, the perfume oil comprises elevating raw materials as defined in WO2012/084916, the content of which is included by reference.

As non-limiting examples one may cite, examples of PRMs meeting any of these criteria can be found in the examples below. In particular, examples of PRMs identified as being Elevating PRMs include isopropylmethyl butyrate, safranal, citronellol, linalool, butyl acetate, alpha-bisabolol, carvone, Exaltolide® (pentadecanolide, origin: Firmenich SA, Geneva, Switzerland), Fructalate® (diethyl 1,4-cyclohexane dicarboxylate, origin: Firmenich SA, Geneva, Switzerland), Koumalactone® ((3aRS,6SR,7aSR)-perhydro-3,6-dimethyl-benzo[B]furan-2-one, origin: Firmenich SA, Geneva, Switzerland), methyl benzoate, dihydroestragole, allyl heptanoate and hydroxycitronellal, among which isopropylmethyl butyrate, safranal, citronellol, butyl acetate, alpha-bisabolol, carvone, Exaltolide® (pentadecanolide, origin: Firmenich SA, Geneva, Switzerland), Fructalate® (diethyl 1,4-cyclohexane dicarboxylate, origin: Firmenich SA, Geneva, Switzerland), Koumalactone® ((3aRS,6SR,7aSR)-perhydro-3,6-dimethyl-benzo[B]furan-2-one, origin: Firmenich SA, Geneva, Switzerland), methyl benzoate and allyl heptanoate are mostly preferred. According to an embodiment, the perfume comprises at least 10% by weight, relative to the total weight of the perfume, of Elevating PRMs. According to an embodiment, the perfume comprises at least 20% by weight, relative to the total weight of the perfume, of Elevating PRMs. According to an embodiment, the perfume comprises at least 30% by weight, relative to the total weight of the perfume, of Elevating PRMs. According to an embodiment, the perfume comprises at least 40% by weight, relative to the total weight of the perfume, of Elevating PRMs. According to an embodiment, the perfume comprises at least 50% by weight, relative to the total weight of the perfume, of Elevating PRMs. According to an embodiment, the perfume comprises at least 60% by weight, relative to the total weight of the perfume, of Elevating PRMs. According to an embodiment, the perfume comprises at least 70% by weight, relative to the total weight of the perfume, of Elevating PRMs. According to an embodiment, the perfume comprises at least 80% by weight, relative to the total weight of the perfume, of Elevating PRMs. According to an embodiment, the perfume comprises at least 90% by weight, relative to the total weight of the perfume, of Elevating PRMs. According to another embodiment, it entirely consists of Elevating PRMs.

Polymeric Shell

The nature of the polymeric shell of the microcapsules of the invention can vary. As non-limiting examples, the shell can be made of a material selected from the group consisting of polyurea, polyurethane, polyamide, polyacrylate, polysiloxane, polycarbonate, polysulfonamide, urea formaldehyde, melamine formaldehyde resin, melamine formaldehyde resin cross-linked with polyisocyanate or aromatic polyols, melamine urea resin, melamine glyoxal resin, gelatin/gum arabic shell wall, and mixtures thereof.

According to an embodiment, the shell of the microcapsule is based on melamine formaldehyde resin or melamine formaldehyde resin cross-linked with at least one polyisocyanate or aromatic polyols.

The shell can also be a hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

According to a particular embodiment, the core-shell microcapsules are cross-linked melamine formaldehyde microcapsules obtainable by a process comprising the steps of:

1) admixing a perfume oil with at least a polyisocyanate having at least two isocyanate functional groups to form an oil phase;
2) dispersing or dissolving into water an aminoplast resin and optionally a stabilizer to form a water phase;
3) adding the oil phase to the water phase to form an oil-in-water dispersion, wherein the mean droplet size is comprised between 25 and 1000 microns, by admixing the oil phase and the water phase;
4) performing a curing step to form the wall of said microcapsule; and
5) optionally drying the final dispersion to obtain a dried core-shell microcapsule;

This process is described in more details in WO 2013/092375 and WO 2015/110568, the contents of which are included by reference.

According to another embodiment the shell is polyurea-based made from, for example but not limited to isocyanate-based monomers and amine-containing crosslinkers such as guanidine carbonate and/or guanazole. Preferred polyurea-based microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to another embodiment, the shell is polyurethane-based made from, for example but not limited to polyisocyanate and polyols, polyamide, polyester, etc.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazole (all percentages being defined by weight relative to the total weight of the colloidal stabilizer). According to another embodiment, the emulsifier is an anionic or amphiphilic biopolymer preferably chosen from the group consisting of gum Arabic, carboxymethyl cellulose, soy protein, sodium caseinate, gelatin, bovine serum albumin, sugar beet pectin, hydrolyzed soy protein, hydrolyzed sericin, Pseudo collagen, Biopolymer SA-N, Pentacare-NA PF, polyvinyl alcohol, modified polyvinyl alcohol, modified starch, modified cellulose, polysaccharides and mixtures thereof mixtures thereof.

According to a particular embodiment, the polyisocyanate is an aromatic polyisocyanate, preferably comprising a phenyl, a toluyl, a xylyl, a naphthyl or a diphenyl moiety. Preferred aromatic polyisocyanates are biurets and polyisocyanurates, more preferably a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N).

According to a particular embodiment, the polyisocyanate is a trimethylol propane-adduct of xylylene diisocyanate (commercially available from Mitsui Chemicals under the tradename Takenate® D-110N).

The preparation of an aqueous dispersion/slurry of core-shell microcapsules is well known from a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of:
1) preparing an oligomeric composition comprising the reaction product of, or obtainable by reacting together
   a) a polyamine component in the form of melamine or of a mixture of melamine and at least one $C_1$-$C_4$ compound comprising two $NH_2$ functional groups;
   b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c) a protic acid catalyst;
2) preparing an oil-in-water dispersion, wherein the droplet size is comprised between 25 and 1000 microns, and comprising:
   i. an oil;
   ii. a water medium
   iii. at least an oligomeric composition as obtained in step 1;
   iv. at least a cross-linker selected amongst
   A) $C_4$-$C_{12}$ aromatic or aliphatic di- or tri-isocyanates and their biurets, triurets, trimmers, trimethylol propane-adduct and mixtures thereof; and/or
   B) a di- or tri-oxiran compounds of formula
      A-(oxiran-2-ylmethyl)$_n$
      wherein n stands for 2 or 3 and 1 represents a $C_2$-$C_6$ group optionally comprising from 2 to 6 nitrogen and/or oxygen atoms;
   v. optionally a $C_1$-$C_4$ compounds comprising two $NH_2$ functional groups;
3) heating said dispersion;
4) cooling said dispersion.
This process is described in more details in WO 2013/068255, the content of which is included by reference.

According to another embodiment, the shell of the microcapsule is polyurea- or polyurethane-based. Examples of processes for the preparation of polyurea- and polyureathane-based microcapsule slurry are for instance described in WO2007/004166, EP 2300146, EP2579976 the contents of which is also included by reference. Typically a process for the preparation of polyurea- or polyurethane-based microcapsule slurry include the following steps:
   a) dissolving at least one polyisocyanate having at least two isocyanate groups in an oil to form an oil phase;
   b) preparing an aqueous solution of an emulsifier or colloidal stabilizer to form a water phase;
   c) adding the oil phase to the water phase to form an oil-in-water dispersion, wherein the mean droplet size is comprised between 25 and 1000 µm, preferably between 100 and 1000 µm;
   d) applying conditions sufficient to induce interfacial polymerisation and form microcapsules in form of a slurry.

According to the invention, it should be understood that, after encapsulation, whatever the nature of the microcapsule(s), the internal core of the capsule is only made of the core oil composed of a perfume oil.

The hair coloring composition of the present invention can contain microcapsules which can vary by the core perfume oil inside them and/or by the wall (different chemistries or same chemistries but different process parameters like cross-linking temperature or duration).

Cationic Coating

According to a particular embodiment of the invention, the microcapsules have an outer coating selected from the group consisting of a non-ionic polysaccharide, a cationic polymer and mixtures thereof.

Such coating will help drive capsule deposition and retention on substrate during the wash process so that a significant part of the capsules which have not been broken during usage/in the wash phase/upon lathering would transfer to the hair and be available for perfume release when the capsules are broken upon rubbing after drying.

Non-ionic polysaccharide polymers are well known to a person skilled in the art. Preferred non-ionic polysaccharides are selected from the group consisting of locust bean gum, xyloglucan, guar gum, hydroxypropyl guar, hydroxypropyl cellulose and hydroxypropyl methyl cellulose.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 2M Dalton.

According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C13S or C17, origin Rhodia).

According to a particular embodiment, microcapsules are polyurea-based microcapsules having a core-shell morphology and comprising
- an oil-based core comprising a perfume;
- a shell consisting essentially of polymerised polyisocyanate formed from at least one polyisocyanate comprising at least three isocyanate functional groups in the absence of a polyamine or an amine, and an emulsifier chosen in the group consisting of gum Arabic, carboxymethyl cellulose, soy protein, sodium caseinate, gelatin, bovine serum albumin, sugar beet pectin, hydrolyzed soy protein, hydrolyzed sericin, Pseudo collagen, Biopolymer SA-N, Pentacare-NA PF, polyvinyl alcohol, modified polyvinyl alcohol, modified starch, modified cellulose, polysaccharides and mixtures thereof and wherein the microcapsules do not comprise a cationic coating.

According to an embodiment, polyurea-based microcapsules are obtained by a process comprising the steps of:
a) admixing a perfume oil with at least one polyisocyanate having at least three isocyanate functional groups to form an oil phase, provided that the oil phase is essentially free from diisocyanate;
b) dissolving an ionic or non-ionic emulsifier in water to form a water phase, wherein the ionic emulsifier is chosen in the group consisting of gum Arabic, carboxymethyl cellulose, soy protein, sodium caseinate, gelatin, bovine serum albumin, sugar beet pectin, hydrolyzed soy protein, hydrolyzed sericin, Pseudo collagen, Biopolymer SA-N, Pentacare-NA PF, and mixtures thereof and wherein the non-ionic emulsifier is chosen in the group consisting of polyvinyl alcohol, modified polyvinyl alcohol, modified starch, modified cellulose, polysaccharides and mixtures thereof;
c) adding the oil phase to the water phase to form an oil-in-water dispersion;
d) applying conditions sufficient to induce interfacial polymerisation and form microcapsules in form of a slurry;
said process being characterized in that:
- the at least one polyisocyanate having at least three isocyanate functional groups is present in an amount comprised between 1 and 15 wt % of the oil phase,
- no substantial amount of amine or polyamine is added at any stage of the process, and
- it does not comprise a further step of adding a cationic polymer to form an outer coating to the microcapsule.

It has been shown that the blooming effect is particularly strong when the microcapsules have a mean size greater than 100 microns.

Therefore, according to a particular embodiment, microcapsules have a mean size greater than 100 microns, preferably between 100 and 500 microns, most preferably between 150 and 500 microns.

According to an embodiment, microcapsules are used in an amount comprised between 0.1% and 10%, preferably between 0.2% and 5% by weight based on the total weight of the composition.

Of course the above concentrations may be adapted according to the olfactive effect desired in each product.

According to the invention, the oxidative hair coloring composition comprises:
(i) an oxidizing phase comprising an oxidizing agent;
(ii) an alkaline phase comprising an alkaline agent, a dye precursor and a coupling compound, and
(iii) core-shell microcapsules having a polymeric shell and a core comprising a perfume oil, said microcapsules having a mean size equal or greater than 25 microns.

The hair coloring composition of the invention is an oxidative hair coloring composition.

By "oxidative hair coloring composition", it is meant a composition comprising two groups of colorless dye molecules: the dye precursor and the coupling agent. Upon reaction with each other through an oxidation process, they form a wide range of colored molecules (dyes) that are then trapped into the hair due their size. In other words, the dye precursor and the coupling compound form an oxidative hair dye in the presence of the oxidizing agent.

"Dye precursor" and "oxidative dye precursor" are used indifferently in the present invention.

Dye Precursors

Dye precursors can be aromatic compounds derived from benzene substituted by at least two electron donor groups such as $NH_2$ and OH in para or ortho positions to confer the property of easy oxidation.

According to an embodiment, dye precursors are chosen in the group consisting of p-phenylene diamine, 2,5-diamino toluene, N,N-bis(2-hydroxymethyl)-p-phenylene diamine, 4-aminophenol, 1,4-diamino-benzene, and mixtures thereof.

The primary dye precursors is used in combination with coupling agents. Coupling agents are preferably aromatic compounds derived from benzene and substituted by groups such as $NH_2$ and OH in the meta position and do not produce color singly, but which modify the color, shade or intensity of the colors developed by the dye precursor.

According to an embodiment, the coupling agent is chosen in the group consisting of resorcinol, 2-methyl resorcinol, 4-chlororesorchinol, 2,5-diamino-toluene, 1,3-diamino-benzene, 2,4-diaminophenoxyethanol HCl, 2-amino-hydroxyethylaminoanisole sulfate, 4-amino-2-hydroxytoluene, and mixtures thereof.

The oxidative dye precursor is preferably used in an amount comprised between 0.001% and 5%, preferably between 0.1% and 4% by weight based on the total weight of the composition.

The use of oxidative dye precursors and coupling agents in hair coloring formulation have been widely disclosed in the prior art and is well-known from the person skilled in the art. One may cite for example EP0946133A1, the content of which is incorporated by reference.

Alkaline Phase

The alkaline phase comprises an alkaline agent, preferably chosen in the group consisting of ammonia hydroxide, ammonia carbonate, ethanolamine, potassium hydroxide, sodium borate, sodium carbonate, triethanolamine and mixtures thereof.

The alkaline agent is preferably used in an amount comprised between 1% and 10%, preferably between 3% and 9% by weight based on the total weight of the composition.

According to the invention, the coupling agent and the dye precursor in an alkaline medium form an oxidative hair dye in the presence of the oxidizing agent.

Oxidizing Agent

The oxidizing agent will supply the necessary oxygen gas to develop color molecules and create a change in hair color. The oxidizing agent should be safe and effective for use in the compositions herein.

Preferably, the oxidizing agents suitable for use herein will be soluble in the compositions according to the present invention when in liquid form and/or in the form intended to be used.

Preferably, oxidizing agents suitable for use herein will be water-soluble. Suitable oxidizing agents for use herein are selected from inorganic peroxygen oxidizing agents, preformed organic peroxyacid oxidizing agents and organic peroxide oxidizing agents or mixtures thereof.

The oxidizing agent is preferably used in an amount comprised between 5 and 30%, preferably between 5 and 25% by weight based on the total weight of the composition.

Optional Components

Components commonly used in cosmetic compositions may be added into the hair coloring composition as defined in the present invention. One may cite for example, surfactants, cationic polymers, oily substances, silicone derivatives, free perfume, preservatives, ultraviolet absorbents, antioxidants, germicides, propellants, thickeners.

According to a particular embodiment, the hair coloring composition comprises one or more quaternary ammonium compounds, preferably chosen in the group consisting of cetyltrimonium chloride, stearyl trimonium chloride, benzalkonium chloride, behentrimonium chloride and mixture thereof to confer hair conditioner benefits.

Quaternary ammonium compounds are preferably used in an amount comprised between 0.1 and 5% by weight based on the total weight of the composition.

Hair Coloring Kit

The permanent hair coloring formulations are generally marketed as two-component kit to avoid that the oxidation reaction takes place before the use.

Thus, another object of the invention is a hair coloring kit comprising:
(i) a first container comprising an oxidizing agent; and
(ii) a second container comprising an alkalizing agent, a precursor dye and a coupling compound;

characterized in that the first and/or the second container further comprises core-shell microcapsules having a polymeric shell and a core comprising encapsulated perfume oil, said microcapsules having a mean size equal or greater than 25 microns.

According to an embodiment, the hair coloring kit comprises:
(i) a first container comprising an oxidizing phase, wherein the oxidizing phase comprises an oxidizing agent; and
(ii) a second container comprising alkaline phase, wherein the alkaline phase comprises an alkalizing agent, a precursor dye and a coupling compound;

characterized in that the oxidizing phase and/or the alkaline phase further comprises core-shell microcapsules having a polymeric shell and a core comprising encapsulated perfume oil, said microcapsules having a mean size equal or greater than 25 microns.

Embodiments described previously for the hair coloring composition also apply for the hair coloring kit.

According to a preferred embodiment, microcapsules are present in the container comprising the alkaline agent.

Method for Coloring Hair

The hair coloring composition compositions according to the present invention can be prepared in accordance with a method well-known in the art.

In order to use the hair coloring composition according to the present invention to hair, it is only necessary to apply the hair dye composition to the hair, allowing the hair to stand, and then washing the hair by using a shampoo. More specifically, a proper amount of the composition is applied to the hair with, for example, a comb or brush, and the hair thus applied is allowed to stand for about 1 to 30 minutes after the application and then washed with the shampoo. Therefore, another object of the invention is a method for coloring hair comprising the step of:
a) applying the hair coloring composition as defined above on hair,
b) allowing the hair to stand, and
c) washing the hair with a shampoo.

As mentioned previously, since hair coloring formulations are generally provided as two-component kit to avoid that the oxidation reaction takes place before the use, the user may need to mix the content of the first container with the content of the second container as defined above in the kit before applying the composition on hair.

EXAMPLES

Example 1

Preparation of Microcapsules

1-A→Microcapsules A (Polyurea-Based—300 Microns)
Microcapsules A were prepared with the following ingredients:

TABLE 1

| Composition of microcapsules A | |
|---|---|
| Ingredient | Capsules A Amount [g] |
| Oil Phase | 33.2 |
| Perfume oil (perfume A) [1] | 29.9 |
| Polyisocyanate [2] | 3.30 |
| Water phase | 66.8 |
| Gum Arabic [3] | 0.97 |
| Water | 65.83 |

1) see Table 2
2) Takenate® D-110N (trimethylol propane adduct of xylylene diisocyanate); origin and trademark from Mitsui Chemicals, 75% polyisocyanate/25% ethyl acetate
3) Gum Arabic; origin and trademark from Alland & Robert

TABLE 2

| Composition of Perfume A | |
|---|---|
| Raw Material | % |
| 2,4-Dimethyl-3-cyclohexene-1-carbaldehyde 1) | 2.3 |
| citronellol BJ | 0.4 |
| Undecavertol | 1.4 |
| delta damascone | 9.8 |

TABLE 2-continued

Composition of Perfume A

| Raw Material | % |
|---|---|
| (3Z)-3-hexen-1-yl (3Z)-3-hexenoate | 0.6 |
| (+−)-4-methylene-2-phenyltetrahydro-2H-pyran | 5.7 |
| (4Z)-4-dodecenal | 0.1 |
| (+−)-(3E)-4-(2,6,6-trimethyl-2-cyclohexen-1-yl)-3-buten-2-one (A) + (3E)-4-(2,6,6-trimethyl-1-cyclohexen-1-yl)-3-buten-2-one (B) | 5.9 |
| Neobutenone ® [2] | 4.3 |
| Nirvanol ® [3] | 0.5 |
| gamma undecalactone | 3.8 |
| Hedione ® [4] | 1.3 |
| Hexyle salicylate | 11.3 |
| Benzyle benzoate | 51.1 |
| Habanolide ® [5] | 1.5 |
| SUM | 100 |

[1] Origin: Firmenich SA, Geneva, Switzerland
[2] 1-(5,5-dimethyl-1-cyclohexen-1-yl)-4-penten-1-one; Origin: Firmenich SA, Geneva, Switzerland
[3] 3,3-dimethyl-5-(2,2,3-trimethyl-3-cyclopenten-1-yl)-4-penten-2-ol; Origin: Firmenich SA, Geneva, Switzerland
[4] Methyl dihydrojasmonate, Origin: Firmenich SA, Geneva, Switzerland
[5] Pentadecenolide Origin: Firmenich SA, Geneva, Switzerland The oil phase was prepared by admixing a polyisocyanate (trimethylol propane adduct of xylylene diisocyanate, Takenate® D-110N, origin and trademark from Mitsui Chemicals) with perfume oil A in the quantities defined in Table 1.

The aqueous phase was prepared by dissolving the gum arabic in water. The emulsion was prepared by dispersing the perfume/polyisocyanate premix oil in the aqueous phase with the stirrer at 230 rpm. pH of the emulsion was measured at 6,7. The temperature was raised to 70° C. and was kept at 70° C. for 1 h30 to allow the curing of the capsules. At this point, capsules were formed, cross-linked and stable. The mixture was left to cool down to room temperature.

After encapsulation and use of the Takenate® D-110N to produce the capsule wall, the residual level of unreacted polyisocyanate in the perfume oil was very low (below 10 ppm) and therefore the internal core of the capsule was essentially made of the perfume oil. The size distribution of the capsules was controlled by Optical Microscopy and Light Scattering (Mastersizer 3000, Malvern) and equals to 300 microns.

1-B→Microcapsules B (Melamine Glyoxal-Based—30 Microns)

In a round bottom flask, melamine (0.8 g), 2,2-dimethoxy-ethanal (60 wt % in water, 1.22 g), glyoxal (40 wt % in water, 1.54 g) and 2-oxoacetic acid (50 wt % in water, 0.52 g) were dispersed in water (2.06 g) at RT. The pH value of the dispersion was controlled with sodium hydroxide (30 wt %, 0.86 g, pH=9.5). The reaction mixture was heated at 45° C. for 25 minutes to give a solution. Then water (6.72 g) was added and the resin was stirred at 45° C. until fully transparent.

Resin was transferred in a 200 mL beaker. Guanazole (0.55 g) was dissolved in a solution of Ambergum 1221 (2 wt % in water, 25.18 g). The resulting solution was introduced into the beaker. An oil solution of Takenate D-110N (1.94 g) and a perfume oil A (composition from TABLE 2) (24.97 g) was added into the aqueous solution. The biphasic reaction mixture was sheared with an Ultra-turrax at 24000 rpm for 2 min. Acetic acid (0.14 g) was added to initiate the polycondensation (pH=5.35). The quality of the emulsion was controlled by light microscopy. The emulsion was transferred into a 200 mL Schmizo reactor and was heated at 45° C. for 1 h, then at 60° C. for 1 h and finally at 80° C. for 30 minutes and coiled to 70° C. over 25 min. A solution of first cationic copolymer namely acrylamidopropyltrimonium chloride/acrylamide copolymer (Salcare SC60, origin BASF) (18.96 g, 3 wt % in water), and second cationic copolymer polygalactomannan 2-hydroxy propyltrimethyl-ammonium chloride ether (Jaguar C13S, origin Rhodia) (9.71 g, 1 wt % in water), was then added and the reaction mixture was heated at 70° C. for 1 h. A solution of urea (4.54 g, 40 wt % in water) was finally added to the reaction mixture, which was heated at 70° C. for 30 min.

The size distribution of the capsules was controlled by Optical Microscopy and Light Scattering (Mastersizer 3000, Malvern) and the mean particle size equals to 30 microns.

1-C→Comparative Microcapsules C (Melamine Glyoxal-Based—10 Microns)

Comparative microcapsules C were prepared by using the same protocol as for capsules B except that they have a mean particle size equals to 10 microns.

Example 2

Olfactive Performance in a Hair Coloring Formulations

TABLE 3

Composition of the alkaline base A

| Ingredients | % |
|---|---|
| Phase A | |
| Water | 44.83 |
| Carbomer [1] | 0.8 |
| p-phenylenediamine [2] | 1 |
| m-aminophenol [3] | 1 |
| m-phenylenediamine sulfate [4] | 0.07 |
| resorcinol [5] | 0.5 |
| Phase B | |
| Laureth-2 [6] | 6 |
| Laureth-12 [7] | 6 |
| Propylene glycol | 6 |
| Glycol distearate [8] | 3.5 |
| Oleth-30 [9] | 3.5 |
| Lauric acid | 3.5 |
| Cetearyl alcohol [10] | 16 |
| Phase C | |
| Ethanolamine | 3.5 |
| Polyquaternium-6 [11] | 2.5 |
| Cetrimonium chloride [12] | 0.3 |
| Pentasodium pentetate [13] | 0.2 |
| Sodium metabisulfite [14] | 0.3 |
| Vitamin C [15] | 0.3 |
| Perfume B [16] | 0.5 |

[1] Carbopol EDT 2050
[2] Covastyle PAP
[3] Covastyle MAP
[4] Covastyle MPDS
[5] Resorcine
[6] Arlypon F
[7] Lipocol L 12
[8] Cutina AGS
[9] Emulgin O 30
[10] Lanette O
[11] Covastyle PAP
[12] Dehyquart A-CA
[13] Dissolvine D-40
[14] Covastyle MBS
[15] Ascorbic Acid
[16] see table 6

Procedure:

All ingredients of Phase A were mixed and heated until 75° C.

All ingredients of Phase B were combined and melt at 70-75° C.

Phase B was added to Phase A (both at 70-75° C.) with good agitation. Mixing was continued until cooled down to 40° C.

Remaining ingredients of Phase C were added under stirring.

TABLE 4

Composition of the alkaline base B

| Ingredients | % |
|---|---|
| Phase A | |
| Water | 39.13 |
| Carbomer [1] | 0.9 |
| p-phenylenediamine [2] | 1 |
| m-aminophenol [3] | 1 |
| m-phenylenediamine sulfate [4] | 0.07 |
| resorcinol [5] | 0.5 |
| Phase B | |
| Propylene glycol | 6 |
| Laureth-2 [6] | 6 |
| Laureth-12 [7] | 6 |
| Dimethicone [8] | 0.7 |
| Phase C | |
| Cetearyl alcohol [9] | 18 |
| Oleth-30 [10] | 3 |
| Lauric acid | 3 |
| Glycol distearate [11] | 3 |
| Phase D | |
| Sodium metabisulfite [12] | 0.4 |
| Silica dimethyl silyate | 0.3 |
| Pentasodium pentetate [13] | 0.2 |
| Polyquaternium-22 [14] | 1 |
| Ammonium Hydroxide [15] | 9.3 |
| Perfume B [16] | 0.5 |

[1] Carbopol Ultrez 10 Polymer
[2] Covastyle PAP
[3] Covastyle MAP
[4] Covastyle MPDS
[5] Resorcine
[6] Lipocol L 12
[7] Arlypon F
[8] Dow Corning 200 Fluid 350
[9] Lanette O
[10] Emulgin O 30
[11] Cutina AGS
[12] Covastyle MBS
[13] Dissolvine D-40
[14] Merquat 280
[15] Ammonium hydroxide 30% aqueous solution
[16] see table 6

Procedure:

All ingredients of Phase A were mixed and heated until 75° C.

All ingredients of Phase B were combined and melt at 70-75° C.

Phase B was added to Phase A (both at 70-75° C.) with good agitation.

Phase C was added while mixing continued until cooled down to room temperature

At room temperature Phase D ingredients were added while mixing

Remaining ingredients of Phase C were added under stirring.

TABLE 5

Composition of the oxidative base C

| Ingredients | % |
|---|---|
| Phase A | |
| Water | 75 |
| Phase B | |
| Cetearyl alcohol and dicethyl phospahate and Cteteth-20 phosphate [1] | 3.5 |
| Mineral oil [2] | 3.5 |
| Cetyl acetate and acetylated lanolin alcohol [3] | 0.35 |
| Steareth-20 [4] | 0.35 |
| Phase C | |
| Hydrogen peroxide [5] | 17 |
| Perfume B [6] | 0.3 |

[1] Crodafos CS 20 Acid
[2] Paraffin Oil 30-40 cPs
[3] Acetulan
[4] Brij 78P
[5] Hydrogen Peroxide 35% aqueous solution
[6] see table 6

Procedure:

All ingredients of Phase A were mixed and heated until 75° C.

All ingredients of Phase B were combined and melt at 70-75° C.

Phase B was added to Phase A (both at 70-75° C.) with good agitation and mixing continued until cooled down to room temperature At room temperature Phase C ingredients were added while mixing

TABLE 6 composition of perfume B

| Raw Material | % |
|---|---|
| (+−)-2,6-DIMETHYL-5-HEPTENAL | 0.1 |
| DIHYDROMYRCENOL | 6.5 |
| CAPROATE ALLYL | 3.9 |
| 2,4-DIMETHYL-3-CYCLOHEXENE-1-CARBALDEHYDE | 0.4 |
| (+−)-3,7-DIMETHYL-3-OCTANOL | 58.9 |
| (2RS,4SR)-4-METHYL-2-(2-METHYL-1-PROPEN-1-YL)TETRAHYDRO-2H-PYRAN (A) + (2RS,4RS)-4-METHYL-2-(2-METHYL-1-PROPEN-1-YL)TETRAHYDRO-2H-PYRAN (B) | 0.1 |
| FLOROL ® 1) | 0.2 |
| ETHYL LINALOOL | 0.3 |
| GERANIOL PUR | 0.3 |
| 4-CYCLOHEXYL-2-METHYL-2-BUTANOL | 2.3 |
| 1-METHOXY-4-[(1Z)-1-PROPEN-1-YL]BENZENE | 1.6 |
| VERDOX™ 2) | 2.4 |
| 3-(4-ETHYLPHENYL)-2,2-DIMETHYLPROPANAL (A) + 3-(2-ETHYL-PHENYL)-2,2-DIMETHYL-PROPANAL (B) | 0.6 |
| SLICYNILE | 5.0 |
| BÉTA IONONE | 0.4 |

TABLE 6-continued composition of perfume B

| Raw Material | % |
| --- | --- |
| BUTYRATE CARBINOL BDM | 0.3 |
| ISOBUTYRATE DE PHENOXY | 1.9 |
| HELIOPROPANAL | 1.3 |
| GAMMA UNDECALACTONE | 0.5 |
| (-)-(2E)-2-ETHYL-4-[(1R)-2,2,3-TRIMETHYL-3-CYCLOPENTEN-1-YL]-2-BUTEN-1-OL | 0.2 |
| HEDIONE ® | 6.7 |
| ALDEHYDE HEXYLCINNAMIQUE | 4.5 |
| EXALTOLIDE | 0.4 |
| MUSCONE | 0.2 |
| 1,4-DIOXACYCLOHEPTA-DECANE-5,17-DIONE | 1.3 |
| SUM | 100 |

1) tetrahydro-2-isobutyl-4-methyl-4(2H)-pyranol, Firmenich SA, Geneva, Switzerland
2) 2-tert-butyl-1-cyclohexyl acetate, International Flavors & Fragrances, USA Microcapsules A, B or C were added to alkaline base B.

2 g of alkaline base B were mixed with 2 g of the oxidative base C and perfume intensity was evaluated:

upon mixing of the 2 bases upon application of the mix on hair with a comb on dry hair after combing Olfactive Performance To measure the olfactive effect of the compositions described in the invention containing fragranced microcapsules, 10 g Caucasian brown hair swatches were used with a length of 20 cm and fixed with a flat metal clip. Caucasian hair, flat bundled, was chosen for this evaluation because Caucasian hair is rather thin in diameter and the application of viscous conditioner compositions can be guaranteed to be more reproducible compared to thick and course Asian hair. After mixing 2 g of the alkaline base B with 2 g of the oxidant base C, 4 g of the coloration products were applied via a flat brush on the swatch that was placed on a glass plate and distributed using a comb. Olfactive evaluation on the swatches was carried out right after the application of the hair colorant by a group of 8 panelists. Evaluation was carried out on coded samples and randomized. The intensity was reported on a scale from 1-7 (1=no odor, 7=maximum odor intensity). The average of 8 panelist evaluations is reported. A high performance of capsules can be considered of intensity values of 5 or above.

Perfume intensity was evaluated:

upon mixing of the 2 bases upon application of the mix on hair with a comb on dry hair after combing Results are shown in the table below.

TABLE 7

Olfactive performance in hair coloring composition

| Perfume & capsule composition in hair colorant phase | Perfume intensity upon mixing of the 2 phases Intensity mix | Perfume intensity upon application of the mix on hair with a comb Intensity | Perfume intensity on dry hair after combing Intensity |
| --- | --- | --- | --- |
| Comparative Perfume B @ 0.5% | 3.5 | 3.75 | 2.5 |
| Comparative Perfume B @ 0.5% + 1% capsules C | 3.5 | 3.75 | 4 |
| Perfume B @ 0.5% + 1% capsules B | 4 | 4.5 | 4.5 |
| Perfume B @ 0.5% + 0.83% capsules A | 5 | 6 | 2.75 |

The same quantity of perfume A (0.25%), when encapsulated into larger capsules is delivering a stronger perfume impact when mechanical shear is applied. For capsules B (30 microns) and A (300 microns), there is already an impact during the mixing stage of the 2 phases but the impact is even stronger upon application of the product onto hair with a comb. While very small capsules C (10 microns) do not seem to bring a benefit versus the reference without capsules, there is already a perfume intensity benefit for the 30 microns capsules B, this benefit being much stronger for the 300 microns capsules A. On dry hair, both capsules C (10 microns) and capsules B (30 microns) give a good perfume boost after combing while the boost is more limited for the very large capsules A (300 microns)

Example 3

Preparation of Microcapsules of Different Size

3-A→Comparative Microcapsules 3A (Polyurea-Based—13 Microns)

Microcapsules 3A were prepared by using the same protocol as described for capsules A in Example 1, except that they have a mean particle size equals to 13 microns and a different perfume C was used, see table 8.

TABLE 8

Composition of Perfume C

| Raw Material | % |
| --- | --- |
| citronellol BJ | 2.1 |
| cyclogalbanate | 4.3 |
| delta damascone | 6.5 |
| Gamma Undecalactone | 15.1 |
| Hedione ® [1] | 10.6 |
| Neobutenone ® | 5.1 |
| Octalynol | 0.3 |
| Rose oxide | 0.5 |
| Rhubofix ® [2] | 0.4 |
| Hexyle salicylate | 18.3 |
| Tetralinol | 24.1 |
| Undecavertol | 1.2 |
| Veloutone | 4.5 |

TABLE 8-continued

Composition of Perfume C

| Raw Material | % |
|---|---|
| Violet BC [3] | 6.8 |
| Zestover [4] | 0.3 |
| SUM | 100 |

[1] methyl 2-((1RS,2RS)-3-oxo-2-pentylcyclopentyl)acetate, Firmenich SA
[2] Spiro[1,4-methanonaphthalene-2(1H),2'-oxirane], 3,4,4a,5,8,8a-hexahydro-3',7-dimethyl, Firmenich SA
[3] (3E)-4-(2,6,6-trimethyl-1-cyclohexen-1-yl)-3-buten-2-one
[4] 2,4-dimethyl-3-cyclohexene-1-carbaldehyde 3-B→Microcapsules 3B (Polyurea-Based—70 Microns)
Microcapsules 3B were prepared by using the same protocol as for capsules 3A except that they have a mean particle size equals to 70 microns.

3-C→Microcapsules 3C (Polyurea-Based—140 Microns)
Comparative microcapsules 3C were prepared by using the same protocol as for capsules 3A except that they have a mean particle size equals to 140 microns.

3-D→Microcapsules 3D (Polyurea-Based—360 Microns)
Comparative microcapsules 3D were prepared by using the same protocol as for capsules 3A except that they have a mean particle size equals to 360 microns.

3-E→Comparative Microcapsules 3D (Melamine Glyoxal-Based—10 Microns)
Microcapsules 3E were prepared by using the same protocol as described for capsules B in Example 1, except that they have a mean particle size equals to 10 microns and a different perfume C was used, see table 8.

3-F→Microcapsules 3E (Melamine Glyoxal-Based—40 Microns)
Comparative microcapsules 3F were prepared by using the same protocol as for capsules 3-E except that they have a mean particle size equals to 40 microns.

Example 5

Olfactive Performance in a Hair Coloring Formulations

Perfume D, see table 13 was added to the hair coloration base described in Example 2.

TABLE 9 composition of perfume D

| Raw Material | % |
|---|---|
| Ethyl 2 methylbutyrate | 1.0 |
| Amyl Acetate | 0.3 |
| Ethyl 2-methyl-pentanoate | 0.6 |
| Pipol Acetate | 0.7 |
| Hexyl Acetate | 2.8 |
| Dihydromyrcenol | 5.2 |
| Zestover [1] | 0.1 |
| Fructone | 2.6 |
| Benzyle Acetate | 1.2 |
| Allyl Heptanoate | 2.0 |
| Terpineol | 0.5 |
| Ethyl Linalool | 5.1 |
| Florol | 4.9 |
| Benzyl Propionate | 0.4 |
| Geraniol | 2.0 |
| Mayol | 4.1 |
| Undecavertol | 2.5 |
| Peranat | 0.5 |
| Verdox ™ [2] | 7.7 |
| Decalactone | 0.6 |
| Citronellyl acetate | 0.9 |
| Vanillin | 2.9 |
| Geranyl Acetate | 3.3 |
| Phenylethyl Isobutyrate | 2.6 |
| Coumarin | 1.5 |
| Verdyle Acetate | 1.4 |
| Allyle Cyclopropionate | 0.9 |
| Ethyl Vanillin | 13.3 |
| Cyclosal | 0.9 |
| Butyrate Carbinol BDM | 2.3 |
| Phenoxyethyl Isobutyrate | 0.3 |
| Verdyl Propionate | 0.3 |
| Heliopropanal [3] | 2.3 |
| Gamma Undecalactone | 13.2 |
| Hedione [4] | 0.3 |
| Iso E Super [5] | 1.2 |
| Ald. hexylcinnamique | 0.5 |
| Ambrox® [6] | 1.4 |
| Habanolide® [7] | 0.3 |
| Benzyl Salicylate | 5.6 |
| Ambrettolide | 0.2 |
| SUM | 100 |

[1] 2,4-dimethyl-3-cyclohexene-1-carbaldehyde
[2] 2-tert-butyl-1-cyclohexyl acetate, IFF
[3] 3-(1,3-benzodioxol-5-yl)-2-methylpropanal
[4] methyl 2-((1RS,2RS)-3-oxo-2-pentylcyclopentyl)acetate, Firmenich SA
[5] 1-(octahydro-2,3,8,8-tetramethyl-2-naphtalenyl)-1-ethanone, IFF
[6] (3ar,5as,9as,9br)-3 a,6, 6,9 a-tetramethyldodecahydronaphtho[2,1-b] furan, firmenich SA
[7] pentadecenolide Microcapsules 3A, 3B, 3C, 3D or 3E were added to alkaline base B.

2 g of alkaline base B were mixed with 2 g of the oxidative base C and perfume intensity was evaluated according to the protocol described previously:

- upon mixing of the 2 bases
- upon application of the mix on hair with a comb
- on dry hair after combing Results are shown in the table below.

TABLE 10

Olfactive performance in hair coloring composition

| Perfume & capsule composition in hair colorant phase | Perfume intensity upon mixing of the 2 phases Intensity | Perfume intensity upon application of the mix on hair with a comb Intensity | Perfume intensity on dry hair after combing Intensity |
|---|---|---|---|
| Comparative Perfume D @ 0.6% | 2.8 | 3 | 1.4 |
| Comparative Perfume D @ 0.6% + 0.3% capsules 3-A Polyurea 13 microns | 2.8 | 3.2 | 1.4 |
| Perfume D @ 0.6% + 0.3% capsules 3-B Polyurea 73 microns | 3.6 | 4 | 2.2 |

TABLE 10-continued

Olfactive performance in hair coloring composition

| Perfume & capsule composition in hair colorant phase | Perfume intensity upon mixing of the 2 phases Intensity | Perfume intensity upon application of the mix on hair with a comb Intensity | Perfume intensity on dry hair after combing Intensity |
|---|---|---|---|
| Perfume D @ 0.6% + 0.3% capsules 3-C Polyurea 140 microns | 4.4 | 5.8 | 2 |
| Perfume D @ 0.6% + 0.3% capsules 3-D Polyurea 360 microns | 3.2 | 6 | 2.75 |
| Comparative Perfume D @ 0.6% + 0.4% capsules 3-E Melamine-glyoxal 10 microns | 2.8 | 3 | 4 |
| Perfume D @ 0.6% + 0.4% capsules 3-F Melamine-glyoxal 40 microns | 2.8 | 3.4 | 5.4 |

The same quantity of perfume A (0.1%), when encapsulated into larger capsules is delivering a stronger perfume impact when mechanical shear is applied. For capsules 3-B (73 microns), 3-C (140 microns) 3-D (360 microns) and 3F, there is already an impact during the mixing stage of the 2 phases but the impact is even stronger upon application of the product onto hair with a brush for capsules 3-C and 3-D which are larger than 100 microns. Melamine-glyoxal capsules of smaller particle size of 40 microns (3-E), give a good perfume boost after combing.

The invention claimed is:

1. An oxidative hair coloring composition comprising:
   (i) an oxidizing phase comprising an oxidizing agent;
   (ii) an alkaline phase comprising an alkaline agent, a dye precursor and a coupling compound; and
   (iii) core-shell microcapsules having a polymeric shell, and a core comprising a perfume oil, said microcapsules having a mean size equal or greater than 25 microns
   wherein an oil-based core comprises:
   25-100 wt % of a perfume oil comprising at least 15 wt % of high impact perfume raw materials having a Log T<−4, and
   0-75 wt % of a density balancing material having a density greater than 1.07 g/cm3.

2. The oxidative hair coloring composition according to claim 1, characterized in that core-shell microcapsules have a mean size between 100 and 500 microns.

3. The oxidative hair coloring composition according to claim 1, characterized in that core-shell microcapsules are added in an amount comprised between 0.1% and 10% by weight based on a total weight of the composition.

4. The oxidative hair coloring composition according to claim 1, characterized in that the polymeric shell of the core-shell microcapsule is made of a material selected from the group consisting of polyurea, polyurethane, polyamide, polyacrylate, polysiloxane, polycarbonate, polysulfonamide, urea formaldehyde, melamine formaldehyde resin, melamine formaldehyde resin cross-linked with polyisocyanate or aromatic polyols, melamine urea resin, melamine glyoxal resin, gelatin/gum arabic shell wall and mixtures thereof.

5. The oxidative hair coloring composition according to claim 1, wherein the microcapsules have a cationic coating.

6. The oxidative hair coloring composition according to claim 1, characterized in that the dye precursor is chosen from the group consisting of p-phenylene diamine, 2,5-diamino toluene, N,N-bis(2-hydroxymethyl)-p-phenylene diamine, 4-aminophenol, 1,4-diamino-benzene, and mixtures thereof.

7. The oxidative hair coloring composition according to claim 1, characterized in that the coupling compound is chosen from the group consisting of resorcinol, 2-methyl resorcinol, 4-chlororesorchinol, 2,5-diamino-toluene, 1,3-diamino-benzene, 2,4-diaminophenoxyethanol HCl, 2-amino-hydroxyethylaminoanisole sulfate, 4-amino-2-hydroxytoluene, and mixtures thereof.

8. The oxidative hair coloring composition according to claim 1, characterized in that the oxidizing agent is hydrogen peroxide.

9. The oxidative hair coloring composition according claim 1, characterized in that the alkaline agent is chosen in the group consisting of ammonia hydroxide, ethanolamine and mixture thereof.

10. The oxidative hair coloring composition according to claim 1, characterized in that the composition further comprises one or more quaternary ammonium compounds.

11. The oxidative hair coloring composition according to claim 1, characterized in that core-shell microcapsules are added in an amount comprised between 0.2% and 5% by weight based on a total weight of the composition.

12. The oxidative hair coloring composition according to claim 1, characterized in that the composition further comprises one or more quaternary ammonium compounds selected from the group consisting of cetyltrimonium chloride, stearyl trimonium chloride, benzalkonium chloride, behentrimonium chloride and mixture thereof.

13. A hair coloring kit comprising the hair coloring composition according to claim 1, the kit comprising:
   (i) a first container comprising an oxidizing agent; and
   (ii) a second container comprising an alkalizing agent, a precursor dye and a coupling compound;
   characterized in that the first container and/or the second container further comprises core-shell microcapsules having a polymeric shell and a core comprising encapsulated perfume oil, said microcapsules having a mean size equal or greater than 25 microns.

14. A method for coloring hair comprising the step of:
   a) applying the oxidative hair coloring composition as defined in claim 1 on hair,
   b) allowing the hair to stand, and
   c) washing the hair with a shampoo.

* * * * *